(12) United States Patent
Valle et al.

(10) Patent No.: US 9,155,615 B2
(45) Date of Patent: Oct. 13, 2015

(54) HINGELESS CARTRIDGE FOR USE WITH AN INTRAOCULAR LENS INJECTOR PROVIDING HAPTIC CONTROL

(71) Applicant: Bausch & Lomb Incorporated, Rochester, NY (US)

(72) Inventors: Moises Valle, Tustin, CA (US); Nathan Belcher, Olivette, MO (US); Sushant Muchhala, Aliso Viejo, CA (US); Will Seo, Laguna Niguel, CA (US); Madhu Ayyagari, Rancho Santa Margarita, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 247 days.

(21) Appl. No.: 13/673,330

(22) Filed: Nov. 9, 2012

(65) Prior Publication Data
US 2014/0135782 A1 May 15, 2014

(51) Int. Cl.
*A61F 2/16* (2006.01)

(52) U.S. Cl.
CPC ............ *A61F 2/1691* (2013.01); *A61F 2/1678* (2013.01); *A61F 2/167* (2013.01); *Y10T 29/49826* (2015.01)

(58) Field of Classification Search
CPC ... A61F 9/0017; A61F 2/1691; A61F 2/1678; A61F 9/007; A61F 2/1664; A61F 2/167; A61F 2/16
USPC ......... 623/6.12; 606/106, 107; 604/57, 59, 64
See application file for complete search history.

(56) References Cited

U.S. PATENT DOCUMENTS

| | | | |
|---|---|---|---|
| 5,474,562 A | 12/1995 | Orchowski et al. | |
| 5,947,976 A | 9/1999 | VanNoy et al. | |
| 6,083,231 A | 7/2000 | VanNoy et al. | |
| 7,458,976 B2 | 12/2008 | Peterson et al. | |
| 2008/0255577 A1 | 10/2008 | Downer et al. | |
| 2009/0204122 A1 | 8/2009 | Ichinohe | |
| 2009/0204123 A1 | 8/2009 | Downer | |
| 2009/0270876 A1* | 10/2009 | Hoffmann et al. | 606/107 |
| 2011/0082463 A1* | 4/2011 | Inoue | 606/107 |
| 2012/0221102 A1 | 8/2012 | Tanaka et al. | |

FOREIGN PATENT DOCUMENTS

| | | |
|---|---|---|
| EP | 1967162 A2 | 9/2008 |
| EP | 1980219 A1 | 10/2008 |
| WO | 96/20662 A1 | 7/1996 |

OTHER PUBLICATIONS

International Search Report and Written Opinion of the International Searching Authority in corresponding PCT Application No. PCT/US2013/069208, completed Feb. 18, 2014 (10 pages).

* cited by examiner

*Primary Examiner* — Victor Nguyen
(74) *Attorney, Agent, or Firm* — Toan P. Vo

(57) ABSTRACT

An intraocular lens ("IOL") cartridge includes an upper wall and a lower wall, together defining a lumen for receiving an IOL. The proximal end of the cartridge has an open slot cut into and through the entire thickness of the upper wall so to allow the leading haptic of the IOL to extend above the upper wall. The cartridge includes a proximal-end feature to facilitate folding of the leading haptic radially inward relative to the optic as the IOL moves into the lumen.

10 Claims, 11 Drawing Sheets

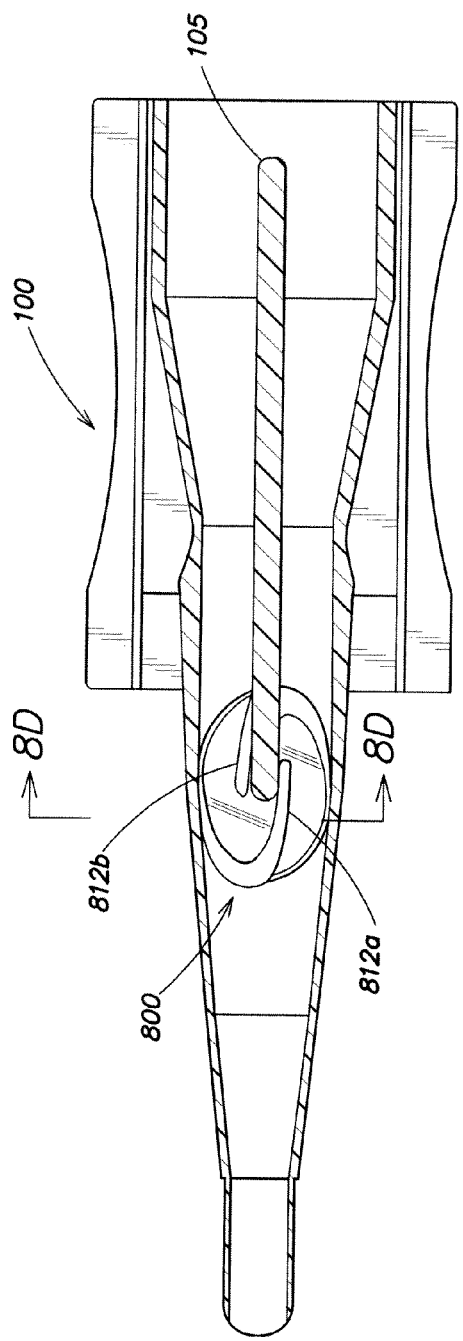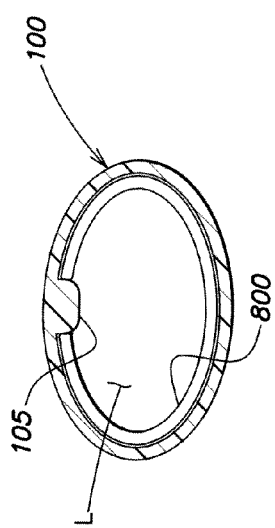
FIG. 8C
FIG. 8D

HINGELESS CARTRIDGE FOR USE WITH AN INTRAOCULAR LENS INJECTOR PROVIDING HAPTIC CONTROL

FIELD OF INVENTION

The present invention relates to injectors for intraocular lenses (IOLs), and methods of using the same.

BACKGROUND OF THE INVENTION

Intraocular lenses (also referred to herein as IOLs or simply as lenses) are artificial lenses used to replace natural crystalline lenses of eyes when the natural lenses are diseased or otherwise impaired. Under some circumstances a natural lens may remain in an eye together with an implanted IOL. IOLs may be placed in either the posterior chamber or the anterior chamber of an eye.

IOLs come in a variety of configurations and materials. Various instruments and methods for implanting such IOLs in an eye are known. Typically, an incision is made in a patient's cornea and an IOL is inserted into the eye through the incision. In one technique, a surgeon uses surgical forceps having opposing blades to grasp the IOL and insert it through the incision into the eye. While this technique is still practiced today, more and more surgeons are using IOL injectors which offer advantages such as affording a surgeon more control when inserting an IOL into an eye and permitting insertion of IOLs through smaller incisions. Smaller incision sizes (e.g., less than about 3 mm) are preferred over larger incisions (e.g., about 3.2 to 5+ mm) since smaller incisions have been associated with to reduced post-surgical healing time and reduced complications such as induced astigmatism.

Injectors come in many configurations, for example an injector may be configured such that the IOL is loaded directly into the body of the injector. Alternatively, an injector may comprises a cartridge into which an IOL is loaded and an injector body into which the cartridge, with the IOL inside, is loaded. The cartridge and/or injector body may be made of disposable or reusable materials.

Conventional IOL cartridges include a load chamber connected to a nozzle. In some configurations, the nozzle includes a small diameter distal tip that is insertable into the eye for delivery of the IOL into the eye. After mating the cartridge with the injector body, a plunger may be translated or screwed through the lumen of the cartridge to urge the IOL through the load chamber and the nozzle into an eye.

In order for an IOL to fit through an incision, it is typically folded and/or compressed prior to entering an eye where it will assume its original unfolded/uncompressed shape. Folding and compression can occur prior to, during or after the IOL is loaded into the cartridge (e.g., using forceps or movement through a tapered nozzle). Since IOLs are very small and delicate articles of manufacture, great care must be taken in their handling, both as they are loaded into an injector and as they are injected into patients' eyes.

It is important that an IOL be expelled from the tip of the IOL injector and into the eye in an undamaged condition and in a predictable orientation. Should an IOL be damaged or expelled from the injector in an incorrect orientation, a surgeon may need to remove or further manipulate the IOL in the eye, possibly resulting in trauma to the surrounding tissues of the eye. To achieve proper delivery of an IOL, consistent loading of the IOL into the injector device with a minimum opportunity for damaging the IOL is desirable.

In general, the IOL is provided to the surgeon in packaging, such as a vial, plastic blister package, or other container for maintaining the IOL in a sterile condition. The IOL is removed from the packaging and loaded into the load chamber of the cartridge prior to insertion into the patient's eye. Removal of the IOL from the packaging and transfer to the load chamber is usually accomplished with forceps or a similar device. The forceps may simply be used to place the IOL on or in the load chamber of the cartridge, or may also fold the IOL to a reduced size for insertion into the eye.

Certain problems may be encountered during delivery of the IOL from the cartridge and into an eye. For instance, during movement though the cartridge lumen, the orientation of the optic and haptic portions may be difficult to control especially if the IOL is folded or compressed inside the nozzle. In addition, problems may be encountered during engagement of the tip of the plunger with the IOL, resulting in damage of optic, haptics, or both.

In view of the above, there is a need for a cartridge that more effectively receives and manages passage of an IOL therethrough.

SUMMARY

Aspects of the present invention are directed to an IOL injector cartridge, comprising an upper wall, a lower wall, the upper wall and the lower wall combining to define a lumen that extends from a proximal end to a distal end, a slot extending through the entire thickness of the upper wall and extending from the proximal end and having a slot distal end formed by the upper wall, an edge of the upper wall that, at least partially defines the slot, having a convex curvature, the curvature occurring along the thickness of the edge.

In some embodiments, the maximum width of the slot is 3.0 mm.

In some embodiments, the slot has a uniform width along a portion of its length. The slot may have a uniform width along substantially its entire length.

In some embodiments, the upper wall has a haptic control feature adjacent the slot.

The slot may be disposed to a side of the centerline of the cartridge.

In some embodiments, the cartridge is in a combination with an injector body comprising a plunger movable along a plunger axis, the cartridge having a longitudinal axis along the centerline of the lumen, the cartridge and injector body connected together such that the plunger axis is laterally biased relative to the cartridge.

In some embodiments, the cartridge is in a combination with an injector body comprising a plunger movable along a plunger axis, the lumen being tilted relative to plunger axis thereby biasing plunger toward the bottom of lumen.

Another aspects of the invention is directed to an IOL injector cartridge, comprising an upper wall, and a lower wall, the upper wall and the lower wall combining to define a lumen that extends from a proximal end to a distal end. There is a slot extending through the entire thickness of the upper wall and extending from the proximal end and having an slot distal end formed by the upper wall, and a haptic control feature proximate the slot.

In some embodiments, an edge of the upper wall that, at least partially defines the slot, has a concave curvature, the curvature occurring along a width of the slot.

The haptic control feature may comprise a shelf.

Another aspect of the invention is directed to a method of loading an IOL having an optic and a leading haptic into a cartridge having a lumen defined, in part, by an upper wall, the upper wall having a slot therein, the method comprises folding the leading haptic by moving the IOL in the lumen with the leading haptic in a slot in a wall of the cartridge as the IOL, the haptic extending over the upper wall.

In some embodiments, the leading haptic is folded to a position over the optic.

In some embodiments, the IOL further comprises a trailing haptic, and wherein the step of folding is performed while the trailing haptic is folded over the optic.

The method may further comprise engaging the IOL with a plunger while the leading haptic is folded.

The method may further comprise engaging the IOL with a plunger while the leading haptic is folded over the optic. In some embodiments, the engaging of the IOL with a plunger occurs while the trailing haptic is folded over the optic.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIGS. 8A, 8B, and 8C illustrate an IOL being inserted into the lumen of a cartridge according to aspects of the present invention. FIG. 8D shows a cutaway cross section of the cartridge and IOL of FIG. 8C taken along line 8D-8D.

DETAILED DESCRIPTION

Figure 1:
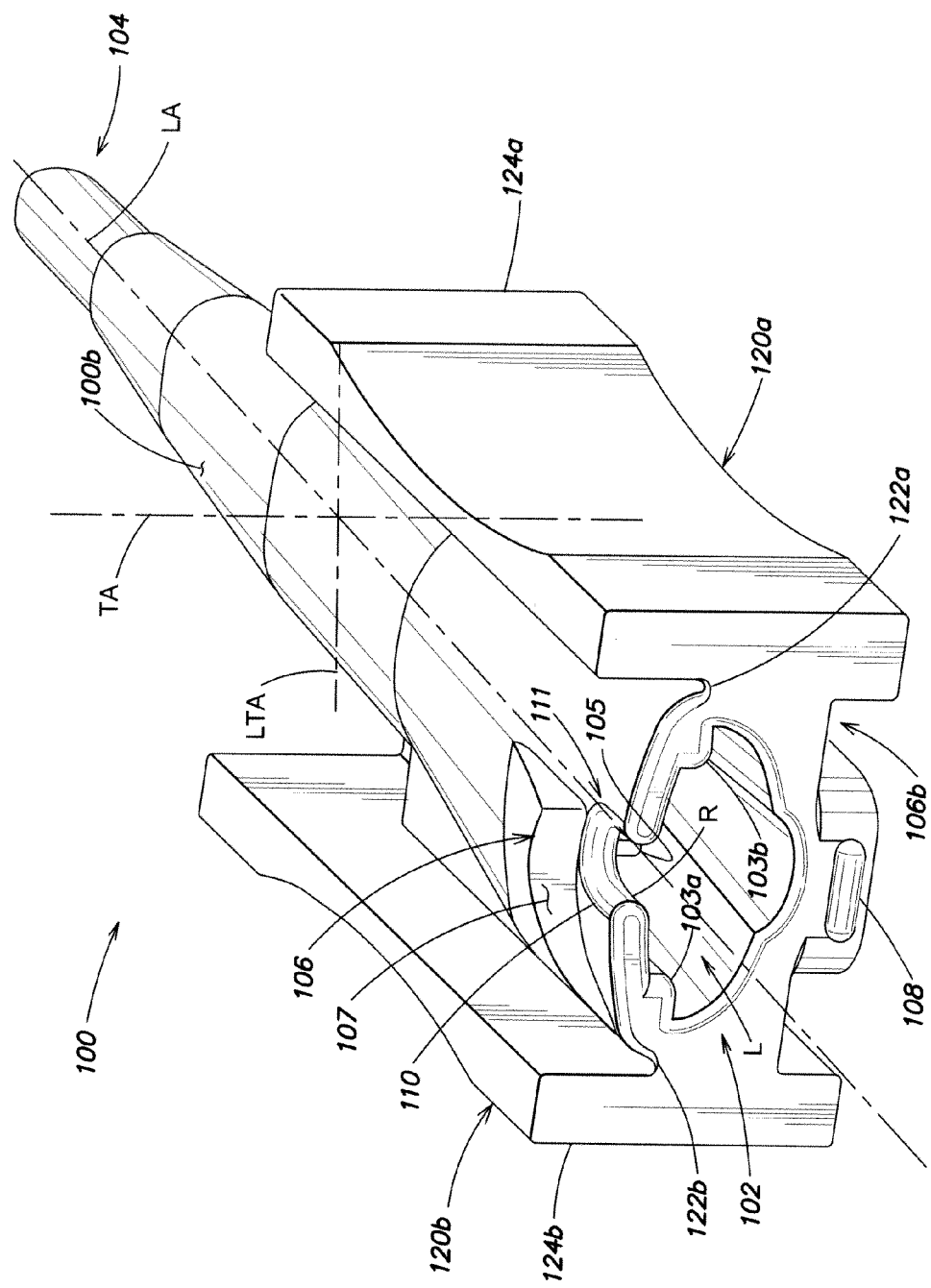
FIG. 1 is a schematic illustration of an example of an embodiment of an intraocular lens injector cartridge according to aspects of the present invention.
Figure 2:
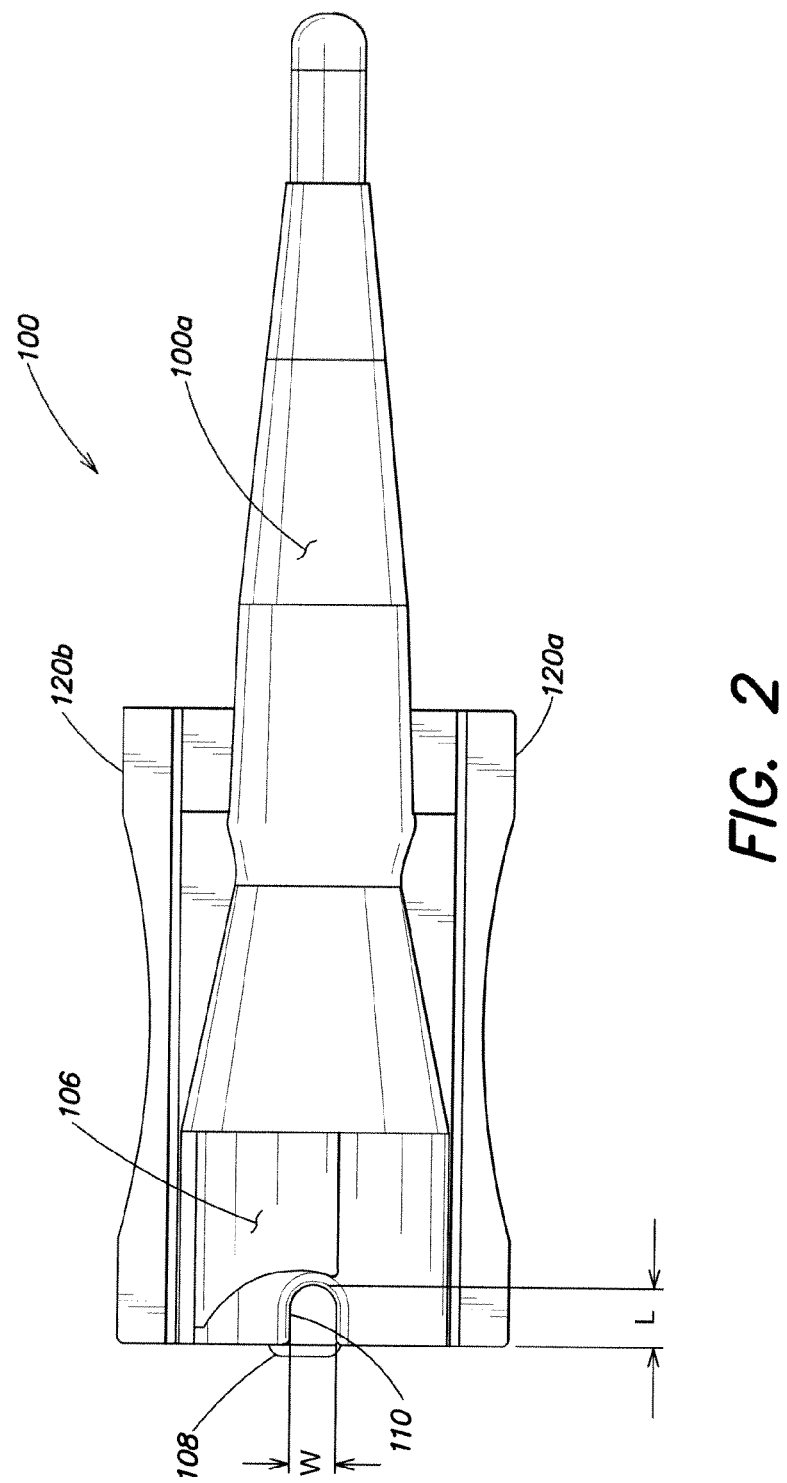
FIG. 2 is a schematic top view of the cartridge illustrated in FIG. 1.
Figure 3:
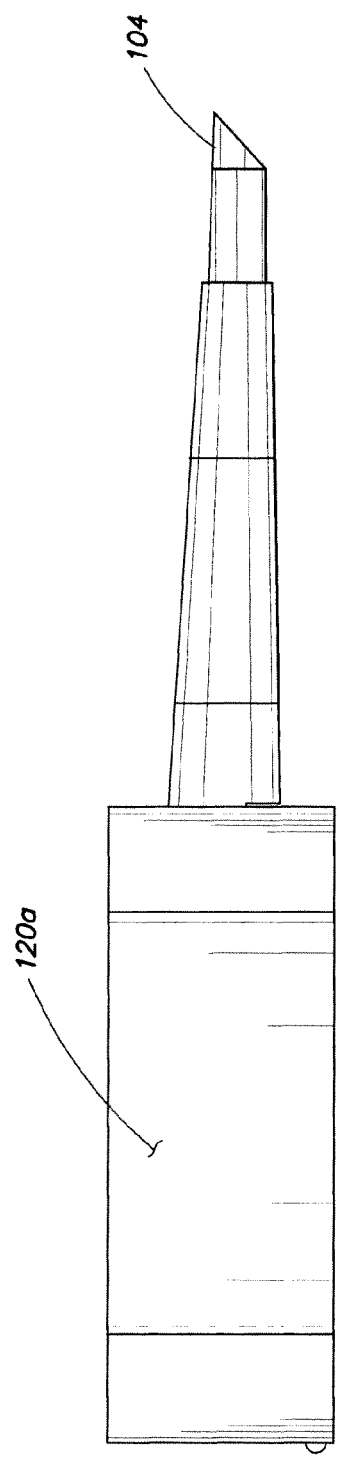
FIG. 3 is a schematic side view of the cartridge illustrated in FIG. 1.
Figure 4:
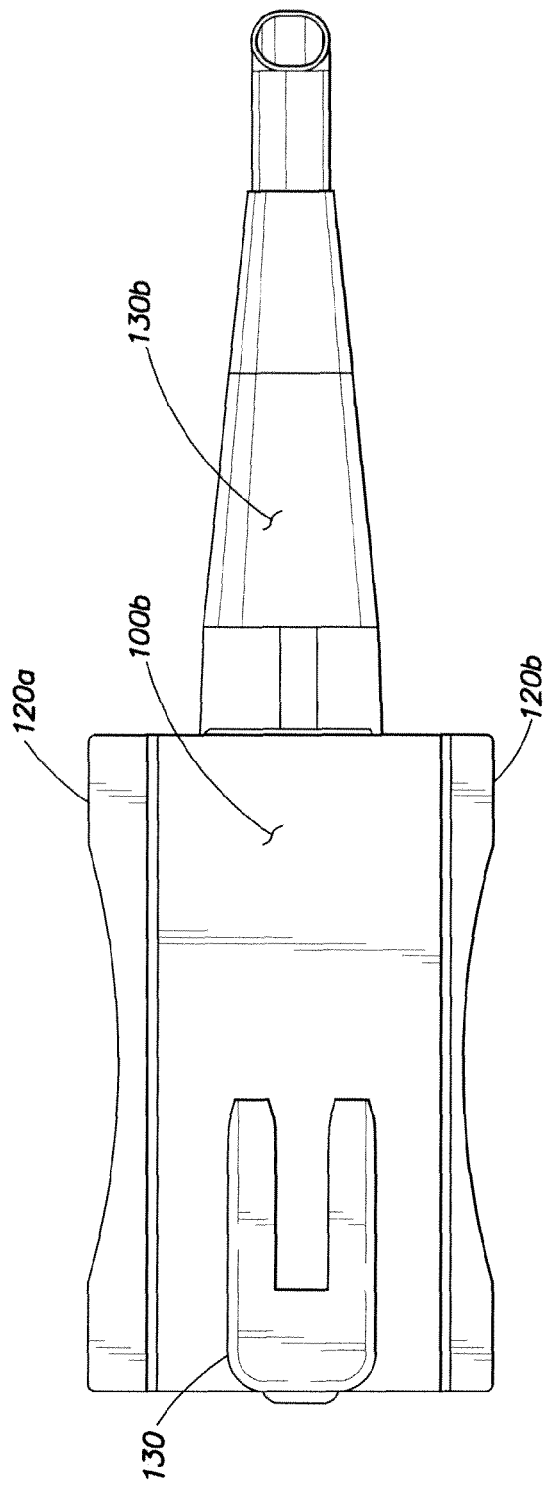
FIG. 4 is a schematic bottom view of the cartridge illustrated in FIG. 1.

Aspects of the present invention are directed towards facilitating injection of an IOL having filament haptics into an eye by using an slot in a wall of a cartridge to fold a leading haptic of an IOL as the IOL is loaded into the cartridge.

An embodiment of an intraocular lens injector cartridge according to aspects of the present invention is discussed below with reference to FIGS. 1-4. IOL injector cartridge 100 comprises an upper wall 100a and a lower wall 100b, the upper wall and the lower wall combine to define a lumen L. The lower wall and upper wall are typically integrated together such as would be formed by a molding process; however, any suitable manufacturing technique may be used and/or multiple components may form a cartridge according to aspects of the present invention. The upper wall refers to the top portion of the cartridge that is facing an operator as the injector is in use delivering a lens into an eye. The lumen extends from a proximal end 102 to a distal end 104. The distal end is typically configured for delivery of the IOL into an eye. However, a cartridge may be configured such that its lumen is aligned with a lumen of an additional component (not shown) of the injector, the additional component being configured for delivery of the IOL into an eye. In the illustrated embodiment, the cross sectional shape of the lumen is oval to constrain the IOL edges (as described below, bumps 103a, 103b are deviations from the oval shape); however a lumen may have a circular or other suitable shape. The cartridge has a longitudinal axis LA extending along the center of the lumen and a transverse axis TA and a lateral axis LTA that are perpendicular to the longitudinal axis.

A slot 110 extends through the entire thickness of the upper wall from the proximal end. The slot has a distal end 111 formed by the upper wall. An edge of the wall that, at least partially, defines the slot has a convex curvature R having its curvature along its thickness. The slot has a width W and a length L. To form the curvature, the edge is curved in the direction of the transverse axis and the curvature is circular, oval or other rounded shape. As described in greater detail below, it will be appreciated that the slot and the edge are sized and shaped to facilitate insertion of an IOL filament haptic into the slot and manipulation of the haptic and the edges are curved to allow manipulation without damaging the haptic.

To provide constraint on the filament haptic during manipulation, the maximum width (substantially in the direction of the lateral axis LTA) of the slot is 3.0 mm or less; it is to be appreciated that, according to aspects of the invention, an injector having a such a slot size can be used regardless of the edge curvature of the slot. To provide a region over which the manipulation can occur, the slot has a uniform width along a portion of its length, and in some embodiments, the slot has a uniform width along substantially its entire length. In such embodiments, it will be appreciated that some narrowing may occur at the distal end of the slot, for example, if the distal end of the slot is curved. Length L is selected to be great enough to maintain the haptic while manipulation occurs (e.g., 0.5-5 mm).

Figure 9:
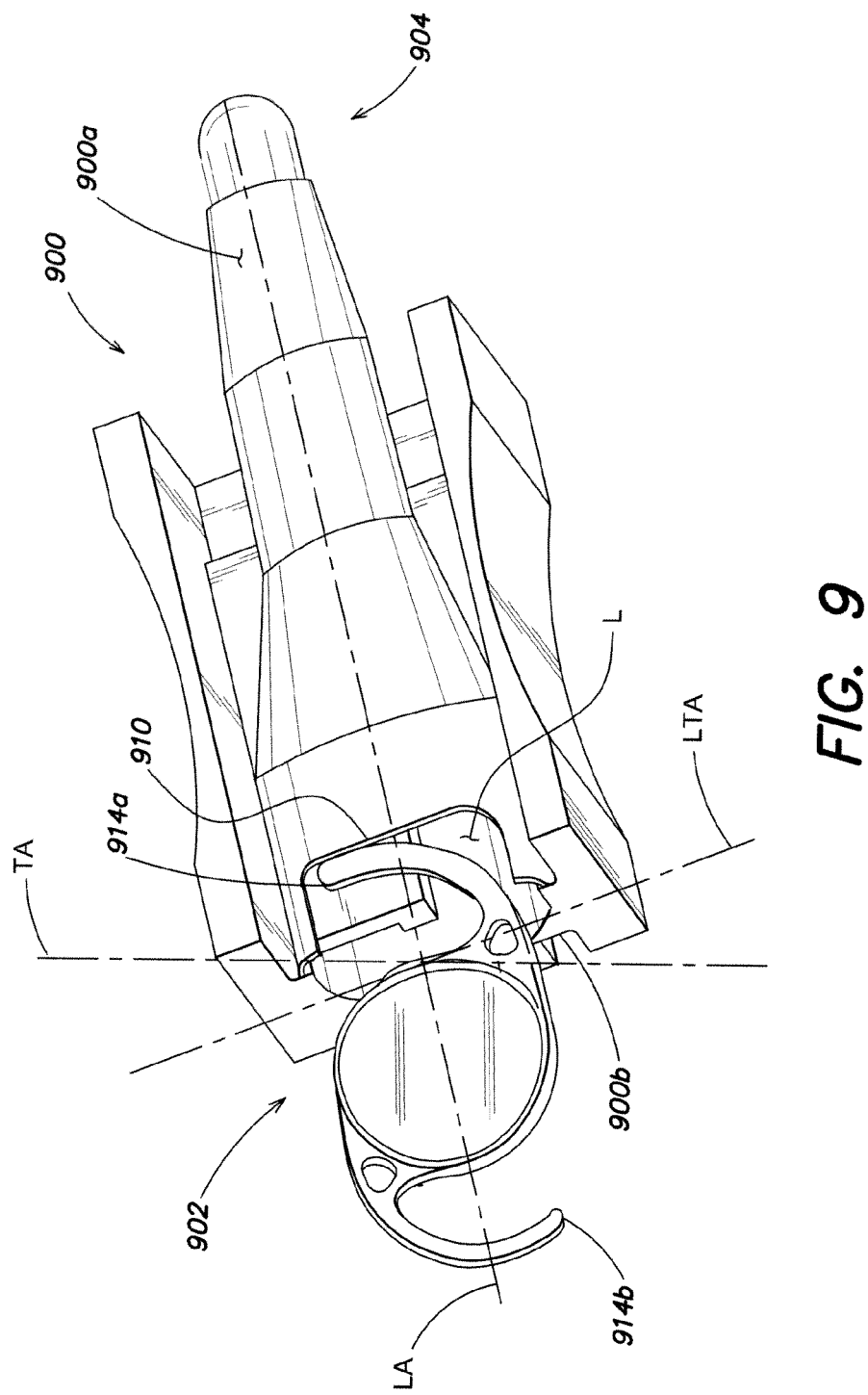
FIG. 9 illustrates another embodiment of an IOL injector cartridge according to aspects of the present invention.

In some embodiments, the upper wall has a haptic control feature 106 proximate the slot (i.e., within a distance equal to the reach of the typical filament haptic of 4.5-6.0 mm). The feature is adapted to help constrain a leading haptic of an IOL during manipulation of the haptic that occurs as the haptic extends through the slot during insertion of the IOL into the cartridge. In some embodiments, such as the one shown in FIG. 1, the control feature comprises a feature extending up from the upper wall thereby forming a sidewall (e.g., sidewall 107) that is typically curved to accommodate a curved filament haptic. Alternatively, the haptic control feature may comprise a shelf and a wall as shown in FIG. 9. The shelf is formed by a reduction in the upper wall height. It will be appreciated that the shelf is a slot that does not extend through the entire thickness of the upper wall.

At the proximal end of the lumen, protrusions 103a, 103b that deviate from the oval shape and that provide a downward-facing, substantially horizontal wall within lumen are provided to control the edges of an IOL that is loaded into the cartridge at the bottom of the lumen. The protusions operate to maintain the lens centered and near the bottom of the lumen L and to prevent rotation of the IOL as the lens proceeds though lumen L, particularly when the haptic is engaged with slot 110. The protrusions extend down the lumen further than the slot (e.g., about a quarter of the length of lumen) and taper toward the lumen wall until a rounded (e.g., oval or circular) shape lumen results.

Figure 5:
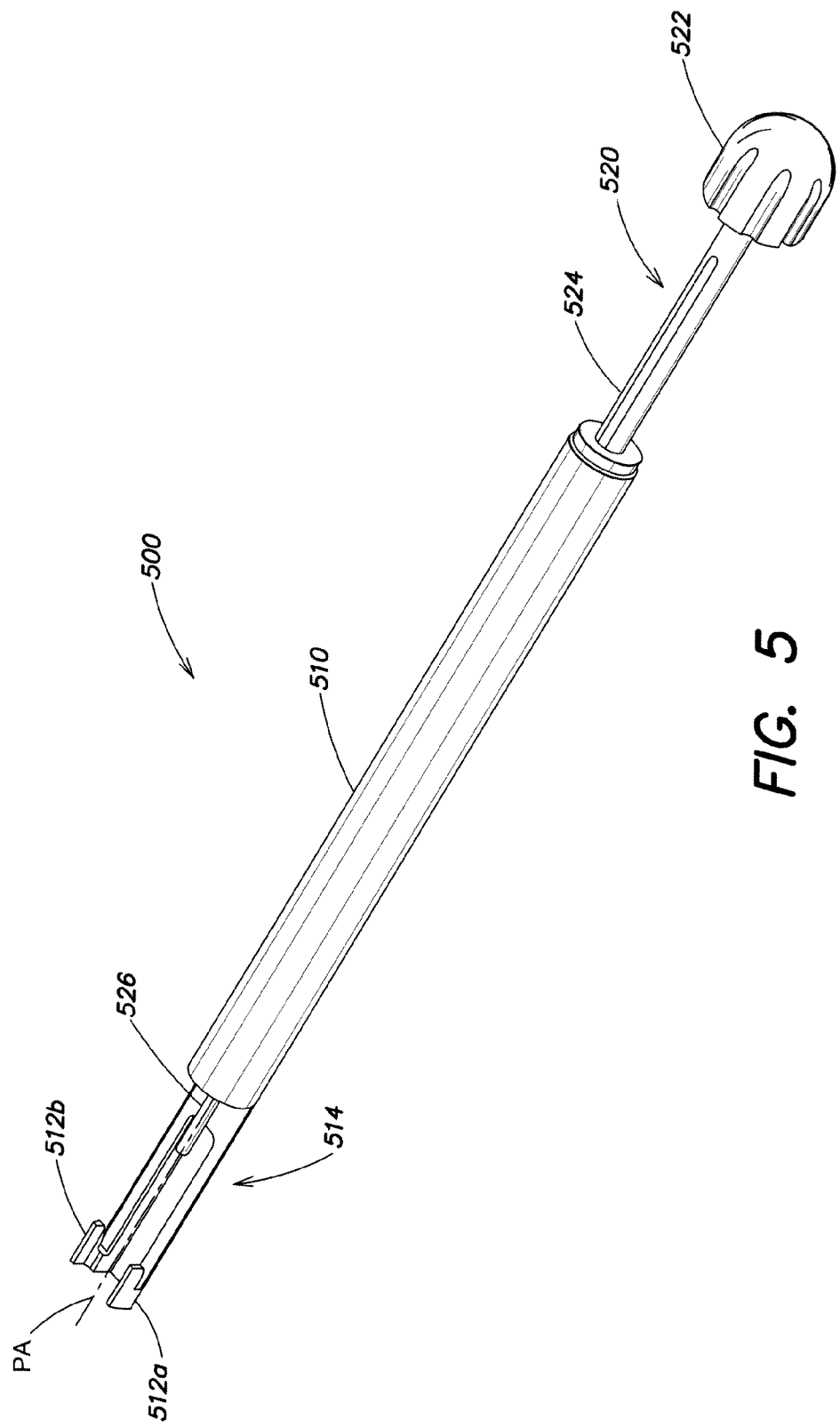
FIG. 5 illustrates an example of an embodiment of an injector body for use with a cartridge according to aspects of the present invention.

Cartridge 100 is provided with an engagement feature 108 for stabilizing the cartridge when it is attached to an injector body (shown in FIG. 5). Wings 120a, 120b are provided to facilitate attachment of the cartridge to the injector body. The wings comprise widened portions 124a, 124b for finger placement during handling to attach the cartridge to the injector body and wastes for attachment to an injector body as set forth below.

Although, in the embodiment illustrated in FIG. 1, slot 110 is located along the centerline of the cartridge (i.e., aligned with the longitudinal axis when the cartridge is viewed from above), in some embodiments the slot is disposed to a side of the centerline of the cartridge (i.e., displaced in the direction of the lateral axis LTA relative to the centerline).

FIG. 5 illustrates an example of an embodiment of an injector body 500 for use with a cartridge according to aspects of the present invention. Injector body 500 comprises a hand piece 510 and a plunger 520. The injector body has a loading area 514 where a cartridge is attached to the injector body. An attachment mechanism 512 is provided at the distal end of the loading area. Although in the illustrated embodiment the attachment mechanism is shown as comprising two prongs 512a, 512b into which frictionally engage the guide wastes 122a, 122b of the cartridge, the cartridge and injector body can be configured to use any suitable technique of attachment (e.g., interference, threading, magnetic).

The plunger 520 operates to urge an IOL present in a cartridge attached the injector body. The plunger comprises a knob 522, a shaft 524 and a distal end 526 having any suitable configuration for engaging an IOL. The plunger moves along a plunger axis PA. Although in the illustrated embodiment, the plunger is configured as a screw-type inserter rotatable using knob 522, the plunger may be simple push rod or other configuration.

Figure 6:
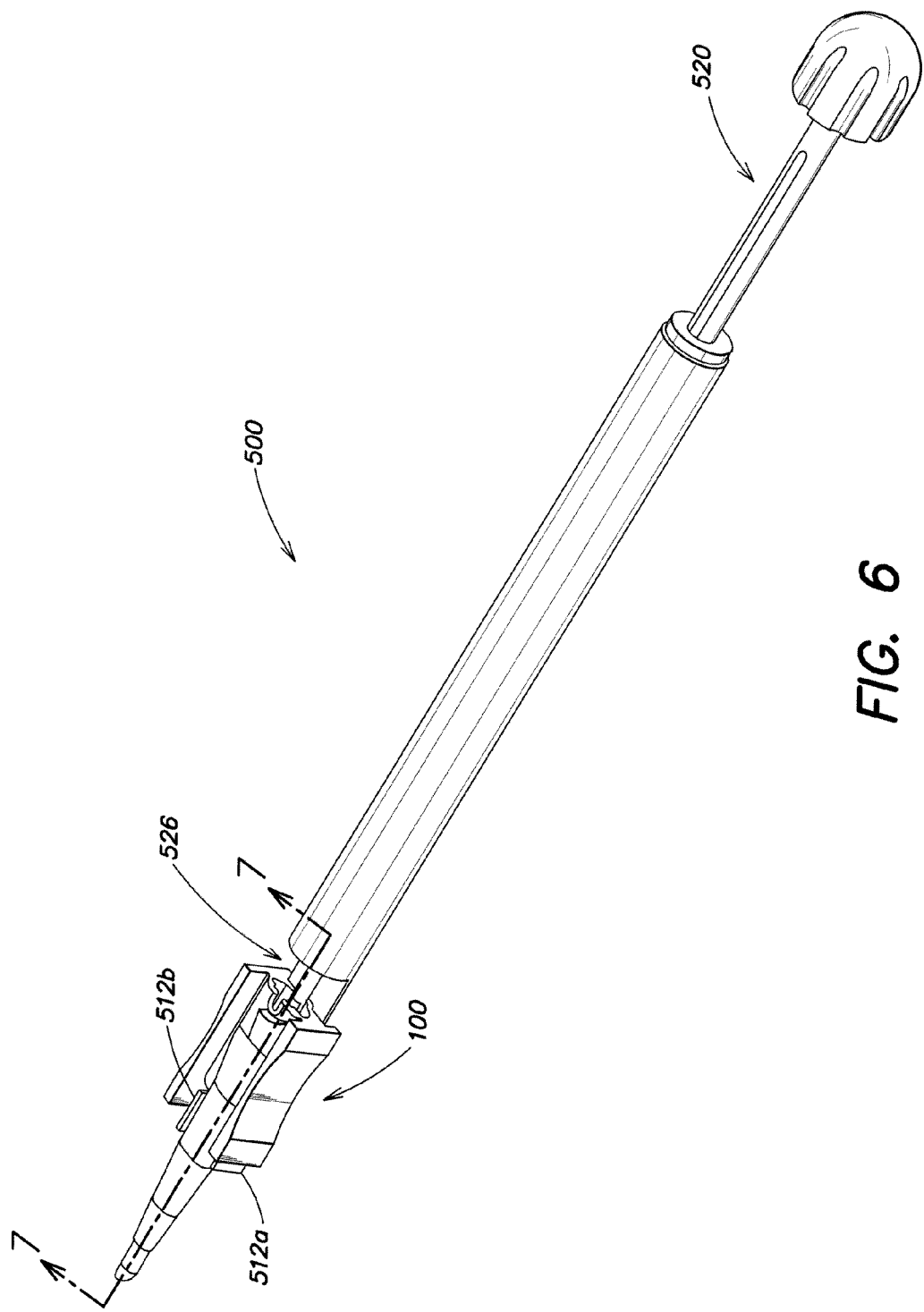
FIG. 6 illustrates the injector body of FIG. 5 in a combination with the cartridge of FIG. 1.

As shown in FIG. 6, the cartridge is inserted into a cartridge reception area at a location proximal to prongs 512a and 512b. The cartridge is then slid distally such that the waists 122a, 122b enter under prongs 512a and 512b and frictionally lock into position under the prongs 512a, 512b.

Figure 7:
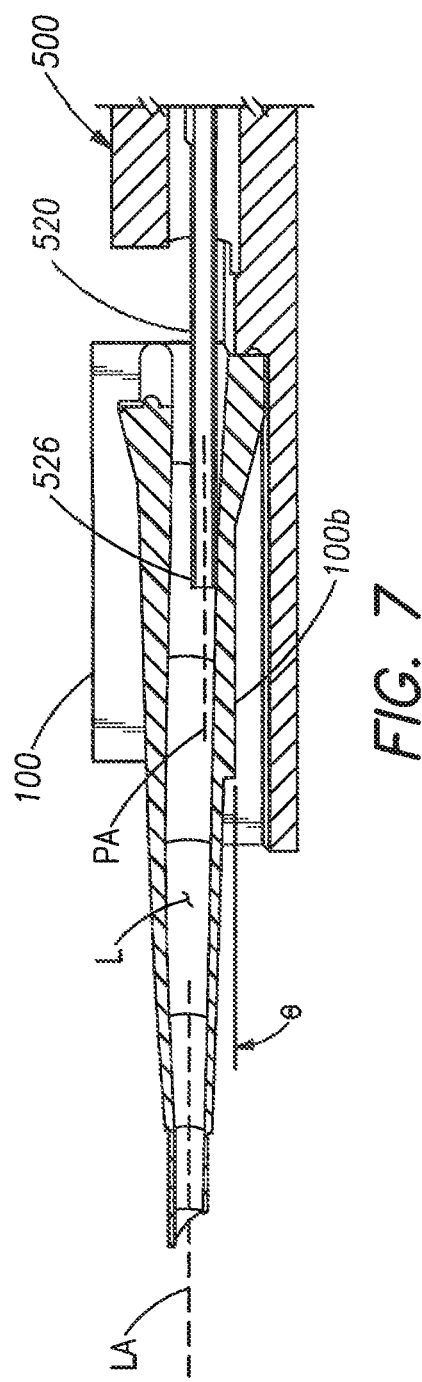
FIG. 7 is a partial cross section of injector body and cartridge taken along line 7-7 in FIG. 6.

FIG. 7 is a partial cross section of injector body 500 and cartridge 100 taken along line 7-7 in FIG. 6 illustrating that, in some embodiments, lower wall 100b has a pitch θ relative to the longitudinal axis such that, when cartridge 100 is assembled with the injector body 500, the lumen is tilted relative to plunger axis PA thereby biasing plunger 520 toward the bottom of lumen L and preventing the plunger from incorrectly contacting IOL. Depending on the pitch and configuration of IOL, such a pitch can be used to contact the IOL optic edge or the haptic.

It will be appreciated that although, in the illustrated embodiment, bottom wall is provided with a pitch, the cartridge and/or injector body may be provided with a pitch such that, when the cartridge is assembled with the injector body, the lumen is tilted relative to plunger axis thereby biasing the plunger toward the bottom or top of the lumen. The direction of the bias is dependent on the shape of the IOL when it is folded and the desired contact location of the plunger on the IOL.

Referring again to FIG. 4, to further bias the plunger (e.g., a lateral bias), a feature 130 is provided on the bottom of the cartridge. Feature 130 is laterally offset relative to the longitudinal axis LA such that, when the cartridge is assembled with an injector body (shown in FIG. 5), the cartridge is offset along the lateral direction relative to the longitudinal axis LA, such that when the plunger (shown in FIG. 5) is actuated, the plunger tip does not travel along longitudinal axis LA, rather the plunger and the plunger axis are disposed to a side of the longitudinal axis of the cartridge. It will be appreciated that a bias can also be achieved by skewing the cartridge relative to the injector body such that, when the cartridge is assembled with an injector body, the cartridge is rotated about transverse axis TA or an axis parallel thereto thereby laterally biasing the plunger tip.

Figure 8A:
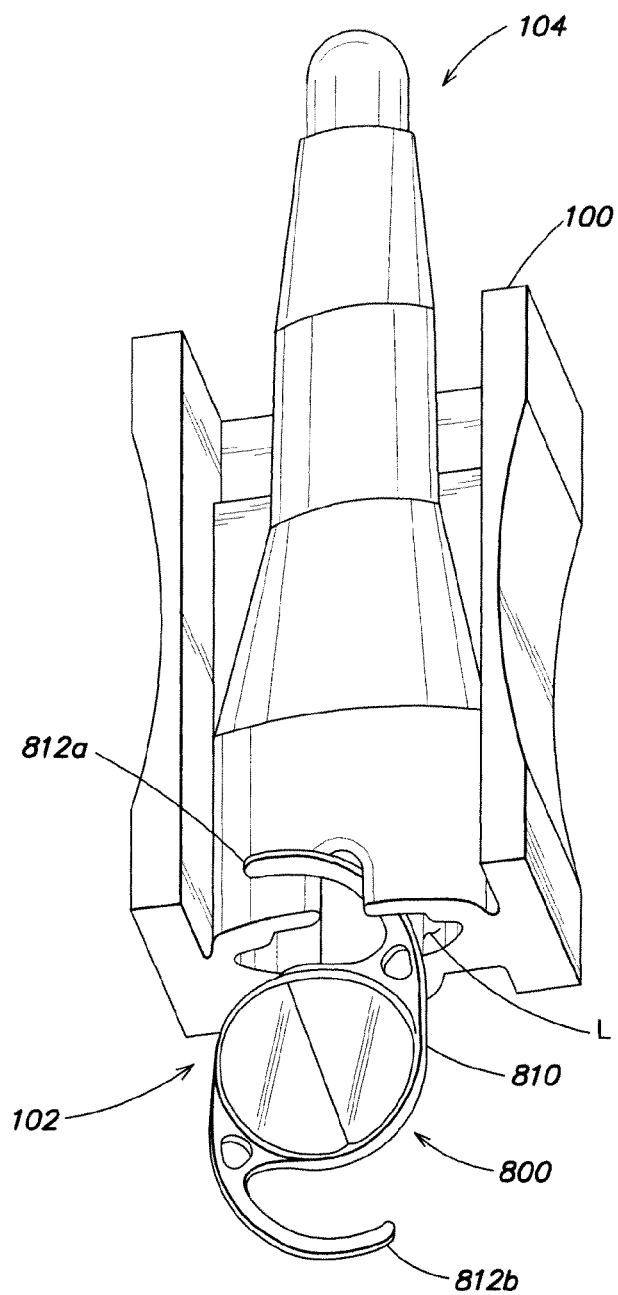

FIG. 8A is an illustration of an IOL 800 being inserted into the proximal end 102 of an injector cartridge 100 lumen L according to aspects of the present invention. IOL 800 comprises haptics 812a, 812b and an optic 810. The haptic that enters lumen L first is referred to as the leading haptic and the haptic that enters lumen L last is the trailing haptic. The optic is inserted into lumen L of cartridge 100 while leading haptic 812a extends up though slot 110. As the IOL moves through the lumen, the leading haptic interferes with the cartridge at the end of the slot and/or along a side of the slot to fold the haptic. The haptic contacts radius R of edge of the upper wall 100a and extends over the top of upper wall 100a.

Figure 8B:
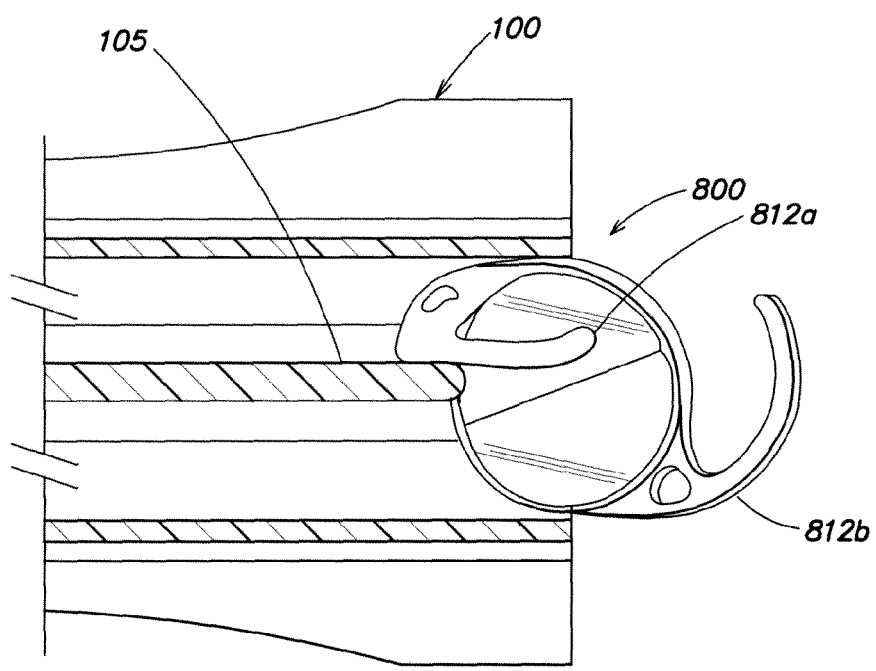

As shown in FIG. 8B, as the IOL is being further inserted into the proximal end of the inserter cartridge, leading haptic 812a is folded to a position over optic 810. Such a configuration provides control and protection of the leading haptic as the IOL proceeds through the lumen and into an eye.

FIG. 8C illustrates IOL 800 at its final position after it has been loaded into the cartridge from the proximal end. For example, IOL may be handled by forceps from the initial entry into the lumen (shown in FIG. 8A) until placement at the final position (shown in FIG. 8C). The IOL remains in the final position until the plunger is actuated to push the IOL out of the distal end of the injector (e.g., the distal end 104 of the cartridge) into an eye. It will be appreciated that the position of leading haptic 812a in a folded position over optic 810 is maintained from the time it is folded by the slot until the final position is attained. Typically, the folded position is further maintained until the IOL is pushed out of the distal end of the injector. As illustrated in FIG. 8C, in some embodiments, it is advantageous if trailing haptic 812b is also folded over the optic when the final position is attained. In some embodiments, the folded position of trailing haptic 812b is attained using forceps or other suitable apparatus prior to entry of the IOL into lumen L; however folding of the trailing haptic may be achieved at any time. Although the illustrated embodiments include only two haptics, an IOL for use with aspects of the present invention may have two or more haptics.

FIG. 8D is a cutaway cross section of the cartridge 100 and IOL of FIG. 8C taken along line 8D-8D. The haptics of IOL 800 are omitted to avoid obfuscation. FIG. 8D shows that, in some embodiments, a ridge 105 is provided on the inner surface of the upper wall that maintains the edges of the IOL in an acceptable position as the IOL is moved through at least a portion of the lumen. An end of ridge 105 is visible in FIG. 1 at the proximal end of the cartridge. It will be appreciated that ridge 105 extends distally further down the lumen than protrusions 103a, 103b, such that after the IOL edges are released from protrusions 103a and 103b, the IOL edges are maintained by ridge 105.

FIG. 9 illustrates another embodiment of an IOL injector cartridge 900 according to aspects of the present invention comprising an upper wall 900a and a lower wall 900b. The upper wall and the lower wall combine to define a lumen L that extends from a proximal end 902 to a distal end 904. A slot 910 extends through the entire thickness of the upper wall, the slot extending from the proximal end of the cartridge and having a slot distal end formed by the upper wall. An edge of the wall, at least partially, defines the slot. The edge has a concave curvature, the curvature occurring along a width of the edge. To form the curvature, the edge is curved in substantially the direction of the lateral axis LTA and has a circular, oval or other rounded shape. As described in greater detail below, it will be appreciated that the slot and the edge are configured to facilitate insertion of a filament haptic 914*a* into the slot and manipulation of the haptic without damaging the haptic. A haptic control feature is located proximate the slot; it is to be appreciated that, according to aspects of the invention, an injector having such a feature can be present regardless of the edge curvature of the slot. In the illustrated embodiment, the haptic control feature comprises a shelf. As described with reference to FIG. 8C above, the trailing haptic 914*b* may be folded or unfolded at the final position prior to actuation of the plunger.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An IOL injector cartridge comprising: an upper wall; a lower wall; the upper wall and the lower wall combining to define a cartridge lumen that extends from a proximal end to a distal end; the upper wall terminating at an upper-wall proximal edge at the proximal end; an open slot being cut into and through the entire thickness of the upper wall, the open slot extending from the upper-wall proximal edge in a direction of a longitudinal axis of the IOL injector cartridge and having a slot distal end intermediate between the proximal end and the distal end of the cartridge; wherein the slot distal end has a convex curvature and at least partially defines the slot; and wherein when an IOL enters the cartridge lumen at the proximal end, a leading haptic of the IOL extends above the upper wall through the open slot.

2. The cartridge of claim 1, wherein the maximum width of the slot is 3.0 mm.

3. The cartridge of claim 1 or 2, wherein the slot has a uniform width along a portion of its length.

4. The cartridge of claim 1 or 2, wherein the slot has a uniform width along substantially its entire length.

5. The cartridge of claim 1, wherein the upper wall has a haptic control feature adjacent the slot.

6. The cartridge of claim 1, wherein the slot is disposed to a side of the centerline of the cartridge.

7. The cartridge of claim 1 in a combination with an injector body comprising a plunger movable along a plunger axis, the cartridge having a longitudinal axis along the centerline of the lumen, the cartridge and injector body connected together such that the plunger axis is laterally biased relative to the cartridge.

8. The cartridge of claim 1 in a combination with an injector body comprising a plunger movable along a plunger axis, the lumen being tilted relative to plunger axis thereby biasing plunger toward the bottom of lumen.

9. The cartridge of claim 1, further comprising two protrusions, each protrusion being disposed to one side of the slot, and each protrusion having a substantially horizontal wall facing the lumen.

10. An IOL injector cartridge comprising: an upper wall; a lower wall, the upper wall and the lower wall combining to define a lumen that extends from a proximal end to a distal end; an open slot extending through the entire thickness of the upper wall and extending from the proximal end and having a slot distal end formed by the upper wall; and the two protrusions, each protrusion being disposed to one side of the slot, and each protrusion having a substantially horizontal wall facing the lumen; wherein a portion of an edge of the upper wall has a convex curvature and at least partially defines the slot; wherein the curvature occurs along the thickness of the edge; and wherein the protrusions extend down the lumen further than the slot and taper toward a lumen wall until a lumen shape becomes rounded.

\* \* \* \* \*